US00PP17739P2

(12) United States Plant Patent
Zerr

(10) Patent No.: US PP17,739 P2
(45) Date of Patent: May 15, 2007

(54) POINSETTIA PLANT NAMED 'FISDRA'

(50) Latin Name: *Euphorbia pulcherrima (Willd. Ex Klotzsch)*
Varietal Denomination: Fisdra

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/347,909

(22) Filed: Feb. 6, 2006

(51) Int. Cl.
*A01H 5/00* (2006.01)

(52) U.S. Cl. ..... Plt./307

(58) Field of Classification Search ..... Plt./303, Plt./307

See application file for complete search history.

*Primary Examiner*—Anne Marie Grunberg
*Assistant Examiner*—S. B. McCormick-Ewoldt
(74) *Attorney, Agent, or Firm*—Jondle & Associates P.C.

(57) ABSTRACT

A new Poinsettia plant particularly distinguished by moderately oak-shaped, light to bright-red bracts with large star-shaped inflorescences, medium green leaves with pointed lobes, an early to mid-season flowering response and a medium to large size, round, and upright plant habit, is disclosed.

1 Drawing Sheet

Genus and species: *Euphorbia pulcherrima* (Willd. Ex Klotzsch).
Variety denomination: 'Fisdra'.

BACKGROUND OF THE NEW PLANT

The present invention comprises a new and distinct cultivar of poinsettia plant, botanically known as *Euphorbia pulcherrima* (Willd. Ex Klotzsch) and hereinafter referred to by the cultivar name 'Fisdra'. The new cultivar originated from a hybridization made in the year 2000 in Hillscheid, Germany. The female parent was the proprietary red-flowered poinsettia plant '9217' (unpatented). The male parent is unknown as the female parent was pollinated with a mixture of pollen from a group of about 50 red-flowered poinsettia plants. The seeds produced by the hybridization were germinated in February 2001. Multiple plants were selected and chosen for asexual propagation in late Summer 2001 and were further evaluated in late Fall 2001. In 2002, the most desirable lines were grafted onto rootstocks of poinsettia plant 'Beckmann's Altrosa' (U.S. Plant Pat. No. 9,336) in order to improve branching ability. Cuttings from the successfully grafted plants were then grown in a trial in the Fall of 2003. A single plant selection was chosen in 2003 and named 'Fisdra'.

The new cultivar was created in 2003 in Hillscheid, Germany and has been asexually reproduced repeatedly by vegetative cuttings in Hillscheid, Germany over a two-year period. 'Fisdra' has not been observed under all possible environmental conditions. The present invention has been found to retain its distinctive characteristics through successive asexual propagations.

Plant Breeder's Rights for this cultivar were applied for in Europe on Feb. 9, 2005 and in Canada on Mar. 18, 2005.

SUMMARY OF THE INVENTION

The following are the most outstanding and distinguishing characteristics of this new cultivar when grown under normal horticultural practices in Hillscheid, Germany.

1. A light to bright-red bract color with no bluish overtone;
2. Large, star-shaped inflorescences with many cyathia and moderately oak-shaped bracts;
3. Medium green leaves with pointed lobes;
4. A medium to large size, upright, well-branched plant habit with rounded foliage canopy; and
5. An early to mid-season flowering response.

DESCRIPTION OF PHOTOGRAPH

This new poinsettia plant is illustrated by the accompanying photograph which shows overall plant habit including blooms, buds, and foliage of the plant; the colors shown are as true as can be reasonably obtained by conventional photographic procedures. The photograph is of a whole plant about 18-weeks old and in full flower, grown in a greenhouse in Langley, British Columbia, in November of 2005.

DESCRIPTION OF THE NEW CULTIVAR

The following detailed description sets forth the distinctive characteristics of 'Fisdra'. The data which define these characteristics were collected from asexual reproductions carried out in Hillscheid, Germany. The plant history was taken on 18-week old plants which were planted as rooted cuttings in 14-cm pots on Jul. 28, 2005 and were pinched on Aug. 12, 2005, which left 7 to 8 leaves remaining. The plants were grown in a greenhouse at a minimum temperature of 18° C. and a ventilation temperature of 24° C. The plants initiated flowers under natural short-day conditions in the Fall. No black cloth was applied to the greenhouse to simulate short-day conditions. No growth regulator was applied. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Euphorbiaceae.
*Botanical.*—*Euphorbia pulcherrima* (Willd. Ex Klotzsch).
*Common name.*—Poinsettia.

Parentage:

*Female parent.*—Red poinsettia plant '9217' (unpatented).

*Male parent.*—Unknown, a mixture of pollen from a group of about 50 red-flowered poinsettia plants.

Growth:

*Form.*—Shrub, self-branching.

*Growth and branching habit.*—Moderately compact structure with medium to strong vigor; pinched plants are bushy with the branches directed upright at an angle of 45° or more; foliage canopy is uniform and rounded.

*Height (from soil line to the top).*—34 cm.

*Width.*—50 cm.

*Time to produce a finished flowering plant.*—About 17 weeks (the total cultivation time) for a 14-cm pot or 9 weeks after the autumnal equinox (late November) when marketable quality is reached.

*Time to initiate and develop roots.*—About 20 days in a greenhouse at 22° C. to 24° C.

Branches:

*Average number.*—7.2.

*Length of branches.*—31 cm to 37 cm.

*Internode length.*—2.5 cm to 3.5 cm.

*Diameter of branches.*—0.7 cm to 0.8 cm.

*Stem color.*—Main part RHS 143B (green); RHS 143C (light-green) near the tips.

Leaves:

*Quantity.*—55 to 65 leaves per plant (8 to 10 leaves per branch).

*Arrangement.*—Alternate.

*Size.*—Length: 13.4 cm. Width: 9.8 cm.

*Shape.*—Ovate.

*Margin.*—Entire.

*Apex.*—Acuminate, relatively long.

*Base.*—Mostly truncate, or weakly rounded.

*Lobes.*—Medium degree, mostly with pointed tips.

*Color (mature leaves).*—Upper surface: Near RHS 137B. Lower surface: RHS 138A.

*Color (immature leaves).*—Upper surface: RHS 143A. Lower surface: RHS 138B.

*Texture.*—Upper surface: Smooth and mostly flat, only weakly veined. Lower surface: Flat and smooth, except for the slightly protruding midrib and finer side veins in a pinnate pattern.

*Venation color.*—Upper surface: RHS 139C (green). Lower surface: RHS 139D (green).

*Variegation.*—None.

*Leaf petiole.*—Length: 7.2 cm. Diameter: 0.2 cm to 0.3 cm. Color: Upper surface: RHS 181A (reddish-brown). Lower surface: RHS 147D (pale-green). Texture: Glabrous.

*Aspect.*—Horizontally to slightly upwardly-directed, the leaf blades slant downward.

Bracts:

*Number per inflorescence.*—12 to 15.

*Shape.*—Ovate.

*Base.*—Rounded.

*Apex.*—Acuminate.

*Lobes.*—Moderate at the larger bracts.

*Size.*—Length: 11.5 cm to 12.5 cm. Diameter: 8.0 cm to 9.0 cm.

*Texture.*—Flat to weakly folded, weak rugosity.

*Bract color.*—Upper surface: RHS 43A (red with a weak orange tone). Lower surface: RHS 52A or lighter (light red/carmine).

*Vein color.*—Upper surface: About RHS 43A (red with a weak orange tone). Lower surface: RHS 49D (pale-pink, nearly white) or RHS 145D (pale-green).

*Bract petiole.*—Length: 0.5 cm to 1.5 cm. Diameter: 0.2 cm to 0.25 cm. Color: Upper surface: RHS 45B (red). Lower surface: Near RHS 49D (pale-pink, nearly white).

Inflorescence:

*Blooming habit.*—Beginning under natural short-day conditions in the Fall: Botanically (cyathia open): Late November. Commercially (bracts colored, marketable): Late November.

*Inflorescence type.*—Medium to large size, star-shaped, with the bracts horizontally directed in a partly overlapping arrangement.

*Average number of inflorescences.*—7.3.

*Lastingness.*—About 4 weeks.

*Diameter.*—27.4 cm.

*Height.*—3.0 cm to 4.0 cm.

Cyme:

*Cyme diameter.*—Up to 3.0 cm.

*Cyathia number.*—10 to 15 in a cluster.

*Cyathium.*—Shape: Ovate. Diameter: 0.5 cm to 0.6 cm. Length: 0.6 cm. Color: Mainly RHS 143C (green); RHS 46C (red) at top.

*Peduncle.*—Color: RHS 145A (light-green). Length: 0.3 cm to 0.5 cm.

*Nectar cups.*—Number: One or two per cyathium. Diameter: 0.4 cm to 0.6 cm. Color: RHS 12A (yellow).

Reproductive organs:

*Stamens.*—Number: 10 to 20 in a cluster. Shape: Strap-like with two anthers. Filaments: Color: RHS 46B (red). Length: 0.3 cm to 0.4 cm. Pollen: Quantity: Moderate (normal). Color: RHS 12A (yellow).

*Gynoecium.*—Not yet observed.

Fruit and seed set: No seed set observed so far.

Disease and insect resistance: No particular resistance or susceptibility has been observed.

COMPARISON WITH PARENTAL AND COMMERCIAL CULTIVARS

'Fisdra' differs from the parental female poinsettia plant '9217' (unpatented) by having light to bright red flowers, while poinsettia plant '9217' has red flowers.

'Fisdra' differs from the commercial cultivar 'Fisnovired' (U.S. Plant Patent applied for), by having medium green foliage compared to the dark green foliage of 'Fisnovired'. Additionally, 'Fisdra' has more vigorous growth and a taller plant habit than 'Fisnovired'.

'Fisdra' differs from the commercial cultivar 'Peterstar' (U.S. Plant Pat. No. 8,259) by having yellow honey cups and fertile stamens, while 'Peterstar' has orange honey cups and stamens that are either missing or abortive without any pollen. Additionally, 'Fisdra' has flatter and less rugose bracts without any bluish hue and more distinct lobed leaves than 'Peterstar'.

I claim:

1. A new and distinct cultivar of Poinsettia plant as shown and described herein.

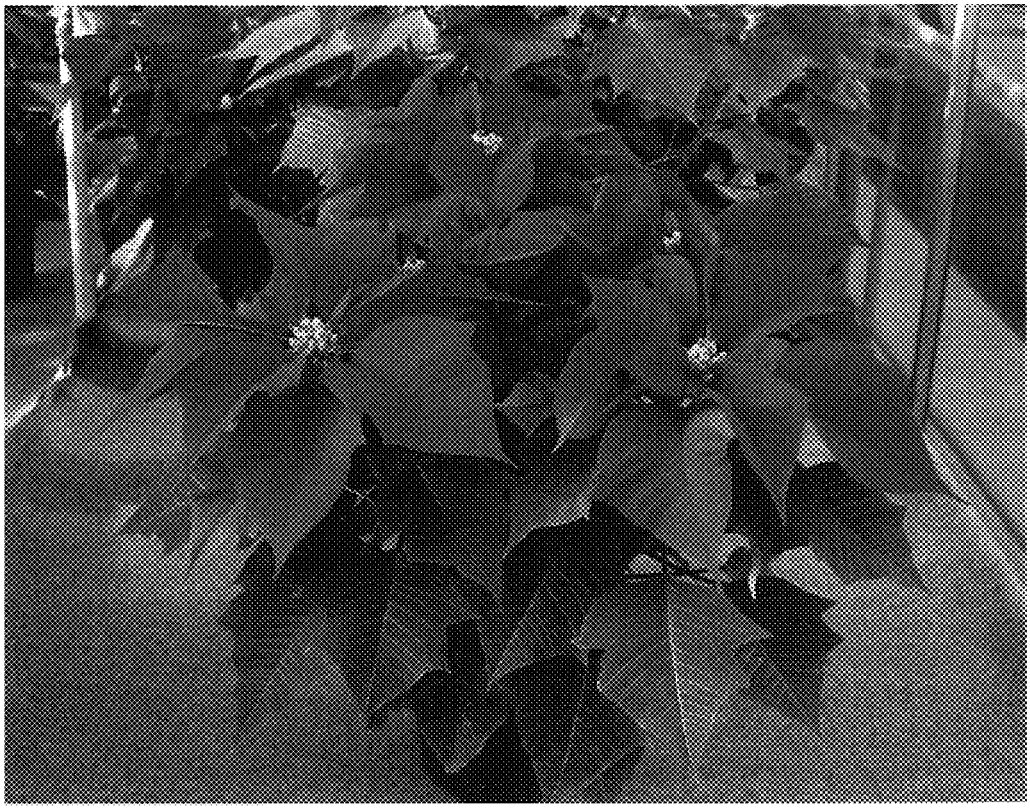

* * * * *